United States Patent [19]

Watson et al.

[11] Patent Number: 5,122,540
[45] Date of Patent: Jun. 16, 1992

[54] METHOD AND COMPOSITION FOR TREATING WARTS AND THROAT SORENESS WITH DMSO AND CITRIC ACID

[75] Inventors: W. Keith R. Watson, 2749 Via Viejas, Alpine, Calif. 92001; Walter B. Dandliker, 1024 Havenhurst Dr., La Jolla, Calif. 92037

[73] Assignees: W. Keith R. Watson; Walter B. Dandliker; William W. Haefliger, all of Pasadena, Calif. ; a part interest

[21] Appl. No.: 468,890

[22] Filed: Jan. 22, 1990

Related U.S. Application Data

[63] Continuation of Ser. No. 830,172, Feb. 28, 1986, abandoned.

[51] Int. Cl.$^5$ .......................................... A01N 37/02
[52] U.S. Cl. ................................... 514/574; 514/936; 514/947
[58] Field of Search ...................... 514/936, 574, 947

[56] References Cited

U.S. PATENT DOCUMENTS

| | | | |
|---|---|---|---|
| 3,551,554 | 12/1970 | Herschler | 424/7.1 |
| 3,743,727 | 7/1973 | Herschler | 424/181 |
| 3,920,835 | 11/1975 | Van Scott | 514/557 |
| 4,234,599 | 11/1980 | Van Scott | 514/557 |
| 4,851,442 | 7/1989 | Watson | 514/553 |
| 4,898,884 | 2/1990 | Watson | 514/553 |

Primary Examiner—Frederick E. Waddell
Assistant Examiner—T. J. Criares
Attorney, Agent, or Firm—William W. Haefliger

[57] ABSTRACT

A solution of DMSO and a body reactive agent (such as citric acid) is provided, and is typically topically applied to the body, as to a wart or to the skin of the throat.

3 Claims, No Drawings

METHOD AND COMPOSITION FOR TREATING WARTS AND THROAT SORENESS WITH DMSO AND CITRIC ACID

This application is a continuation of Ser. No. 830,172, filed Feb. 28, 1986, l now abandoned.

BACKGROUND OF THE INVENTION

This invention relates generally to remedial treatment for sore throat caused by bacterial or viral infection, and to remove wart (papilloma) tissue, more particularly, it concerns compositions and methods for such treatments.

There exists a long recognized need for techniques or processes which will alleviate sore throat, or will remove wart (verruca) tissue including root structure. Current remedies are less than satisfactory.

SUMMARY OF THE INVENTION

It is a major object of the invention to provide method and composition that will meet the above need.

Basically, the method of treating a virus caused benign wart (for example exposed at the skin) on a human or animal patient includes the steps:

a) forming a solution composition consisting essentially of dimethyl sulfoxide and an ingredient dissolved therein, said ingredient selected from the group consisting of citric acid and citric acid monohydrate;

b) topically applying said solution composition to the wart for a period of time and in an amount sufficient to penetrate the wart and to remove wart tissue subsequently.

The solution composition is typically formed by combining between about 10 to 60 weight percent of said ingredient and between about 80 to 40 weight percent dimethyl sulfoxide; and more specifically, the preferred solution consists essentially of about 70 weight percent dimethyl sulfoxide, and about 30 weight percent of said ingredient. A small amount of lidocaine hydrochloride (0.01 to 3.9 weight percent) may be added, or included. A preferred amount of lidocaine hydrochloride is 0.1 weight percent.

EXAMPLE I 70 (or about 70) weight parts of liquid dimethyl sulfoxide are combined with 30 (or about 30) weight parts of citric acid and stirring is continued (30 to 60 minutes) to form the product solution, the solution temperature being between 95° F. to 115° F. A small amount (drop) of the resultant solution is then applied locally and topically to the exposed surface of a papilloma. After several such treatments carried out over several days (5, for example) the wart (papilloma) is easily removable from its position in the skin and subcutaneous tissue, as by lifting. The treatment may be continued for as long as necessary to enable such removal. Since the dimethyl sulfoxide component causes citric acid penetration deeply into the wart, its root structure, containing the viral agent causing the wart, is also removable, the citric acid chemically attacking the embedded viral agent, for example to destroy same.

EXAMPLE II

Same as Example I, except the weight percentages are about as follows:
90 weight % dimethyl sulfoxide
10 weight % citric acid

EXAMPLE III

Same as Example I, except the weight percentages are about as follows:
40 weight % dimethyl sulfoxide
60 weight % citric acid

EXAMPLES IV, V and VI

Same as Examples I-III, except that citric acid monohydrate is substituted for citric acid.

EXAMPLES VII-XII

Same as Examples I-VI, except that between 0.01 to 4.0 weight percent (and preferably about 0.1 weight percent) lidocaine hydrochloride is added to the composition and dissolved therein during said mixing, the relative weight percentages of the dimethyl sulfoxide and citric acid, or citric acid monohydrate remaining the same in the solution.

The method of treating a human or animal patient afflicted with sore throat (inflamed or painful throat-tissue) caused by bacterial or viral infection, includes the steps:

a) forming a solution composition consisting essentially of dimethyl sulfoxide and an ingredient dissolved therein, said ingredient selected from the group consisting of citric acid and citric acid monohydrate; and b) topically applying said solution composition to the patient's neck proximate to the sore area of the throat for a period of time and in an amount of sufficient to alleviate said sore throat.

The solution composition is typically formed by combining between about 10 to 60 weight percent of said ingredient and between about 80 to 40 weight percent dimethyl sulfoxide; and more specifically, the preferred solution consists essentially of about 70 weight percent dimethyl sulfoxide, and about 30 weight percent of said ingredient. A small amount of lidocaine hydrochloride (0.01 to 3.9 weight percent) may be added or include, for rapid sore throat pain suppression. A preferred amount of lidocaine hydrochloride is 0.1 weight percent.

EXAMPLE I'

70 (or about 70) weight parts of liquid dimethyl sulfoxide are combined with about 30 weight parts of citric acid, and the mix is stirred (30-60 minutes) to dissolve the citric acid into the dimethyl sulfoxide, forming the product solution. A small amount (film) of the resultant solution is applied to the patient's neck region, as to the skin proximate to the carotid artery, and over an area of about 1 square inch (½ to 2 square inches also being usable). After one or more such treatments, substantial relief of throat soreness is experienced, such relief continuing for at least several hours (3-10 for example).

After treatment as described, such relief has been experienced, by over fifteen human patients who were suffering severely from such sore throat.

It is believed that the citric acid is carried into the throat tissue by the dimethyl sulfoxide penetrant, to destroy virus and/or bacteria which cause throat inflammation or soreness, such bacteria and virus being normally otherwise protected against treatment via the mouth, by mucuous lining of the throat.

EXAMPLE II'

Same as Example I', except the weight percentages are about as follows:

90 weight % dimethyl sulfoxide
10 weight % citric acid

EXAMPLE III'

Same as Example I', except the weight percentages are about as follows:

40 weight % dimethyl sulfoxide
60 weight % citric acid

EXAMPLES IV', V' AND VI'

Same as Examples I', II' and III', except that citric acid monohydrate is substituted for citric acid.

EXAMPLES VII'-XII'

Same as Examples I'-VI' except that between 0.01 to 4.0 weight percent (and preferably about 0.1 weight percent) lidocaine hydrochloride is added to the composition and dissolved therein during said mixing, the relative weight percentages of the dimethyl sulfoxide and citric acid, or citric acid monohydrate remaining the same in the solution, which is essentially anhydrous.

Reaction products are carried away to the kidneys in body fluid, such as blood.

In the above, if the weight percent of dimethyl sulfoxide is below about 40%, the tissue penetrating capability of the solution is too low for sufficiently effective results; and if the citric acid and or monohydrate weight percent is below about 10%, the virus destroying capability of the solution is insufficient.

We claim:

1. The method for producing and using a solution useful for treating a human or animal patient afflicted with sore throat caused by bacterial or viral infection by topically applying said solution to the patient's neck proximate to the sore area of the throat for a period of time and in an amount sufficient to alleviate said sore throat, which method comprises:
    a) forming said solution consisting of a mixture of dimethyl sulfoxide and citric acid or citric acid monohydrate, by combining between about 10 to 60 weight percent of said citric acid or citric acid monohydrate and between about 90 to 40 weight percent dimethyl sulfoxide, and between 0.1 and 4.0 weight percent lidocaine hydrochloride,
    b) and mixing said citric or citric acid monohydrate and dimethyl sulfoxide and said lidocaine hydrochloride during the formation of said solution, and in the presence of heating, for a time to complete the forming of the solution,
    c) and using said solution, after said step b), by topically applying same to the neck and in amount and for a time as aforesaid.

2. The method of claim 1 wherein said solution consists essentially of about 70 weight percent dimethyl sulfoxide, and about 30 weight percent of said citric acid or citric acid monohydrate, and said 0.1 to 4.0 weight percent lidocaine hydrochloride.

3. The solution of claim 1 which contains about 70 weight percent dimethyl sulfoxide, about 29.9 weight percent said citric acid or citric acid monohydrate, and about 0.1 weight percent lidocaine hydrochloride.

* * * * *